United States Patent [19]
Todd

[11] Patent Number: 5,823,204
[45] Date of Patent: Oct. 20, 1998

[54] PROCESS FOR CRIMPING AND TATTOOING HAIR

[75] Inventor: Mark D. Todd, 1815 Lake Rd., Webster, N.Y. 14580

[73] Assignee: Mark D. Todd, Webster, N.Y.

[21] Appl. No.: 926,347

[22] Filed: Sep. 9, 1997

Related U.S. Application Data

[63] Continuation-in-part of Ser. No. 901,815, Jul. 28, 1997.

[51] Int. Cl.[6] ...................................................... A61K 7/13
[52] U.S. Cl. ........................... 132/208; 132/206; 132/211
[58] Field of Search .................................... 132/206, 207, 132/208, 221, 223, 224, 225, 319; 606/116

[56] References Cited

U.S. PATENT DOCUMENTS

| | | | |
|---|---|---|---|
| D. 315,968 | 4/1991 | Rizzuto et al. ........................... | D28/35 |
| 1,709,981 | 4/1929 | Headington ............................. | 132/225 |
| 2,274,170 | 2/1942 | Stanley .................................... | 132/221 |
| 2,705,499 | 4/1955 | Breeze .................................... | 132/207 |
| 3,433,232 | 3/1969 | Garrett .................................... | 132/208 |
| 4,739,151 | 4/1988 | Smal ....................................... | 132/225 |
| 5,470,351 | 11/1995 | Ross et al. ............................. | 132/319 |

FOREIGN PATENT DOCUMENTS

| | | | |
|---|---|---|---|
| 341869 | 1/1931 | United Kingdom ................... | 132/224 |

*Primary Examiner*—Todd E. Manahan
*Attorney, Agent, or Firm*—Jaeckle Fleischmann & Mugel, LLP

[57] ABSTRACT

A process for removably applying coloring material to hair comprises contacting a composite fabric material to hair and compressing the hair along with the composite material while heating the hair to a temperature of at least 140 degrees Fahrenheit. The composite fabric material is a laminated structure formed from a fiberglass substrate having polytetrafluoroethylene bonded thereto. The top surface of the polytetrafluoroethylene has a water-soluble coloring material deposed thereon which is brought into contact with the hair. The hair is compressed and heated using a hair crimping device with a first jaw with a female die member is attached thereto and a second jaw with a corresponding male die member is attached thereto.

12 Claims, 5 Drawing Sheets

PROCESS FOR CRIMPING AND TATTOOING HAIR

CROSS-REFERENCE TO RELATED PATENT APPLICATION

This application is a continuation-in-part of applicant's copending patent application U.S. Ser. No. 08/901,815, filed on Jul. 28, 1997.

FIELD OF THE INVENTION

A process for transferring coloring agent from a fabric to hair.

BACKGROUND OF THE INVENTION

U.S. Pat. No. Design 315,968 of Leandro P. Rizzuto et al. discloses a hair crimping head appliance comprising a male portion and a female portion. The male portion of the device depicted comprises a protruding heart-shaped die; the female portion of the device comprises a heart-shaped recess which extends through the entire thickness of the female die plate.

However, the device of the Rizzuto et al. patent is not adapted to produce a sharply-defined colored crimped impression in a user's hair.

It is an object of this invention to provide a device which is adapted to produce such colored, sharply-defined, crimped, hair impression.

It is another object of this invention to provide a process for transferring coloring agent from fabric to hair.

SUMMARY OF THE INVENTION

In accordance with this invention, there is provided a process for transferring coloring agent from a fabric to hair in which a composite fabric containing polytetrafluoroethylene and fiberglass which is coated with coloring agent is contacted with hair and heated to a temperature of at least about 140 degrees Fahrenheit.

BRIEF DESCRIPTION OF THE DRAWINGS

The invention will be illustrated by reference to the specification and the following drawings, in which like numerals refer to like elements, and in which.

DESCRIPTION OF THE PREFERRED EMBODIMENTS

Figure 1:
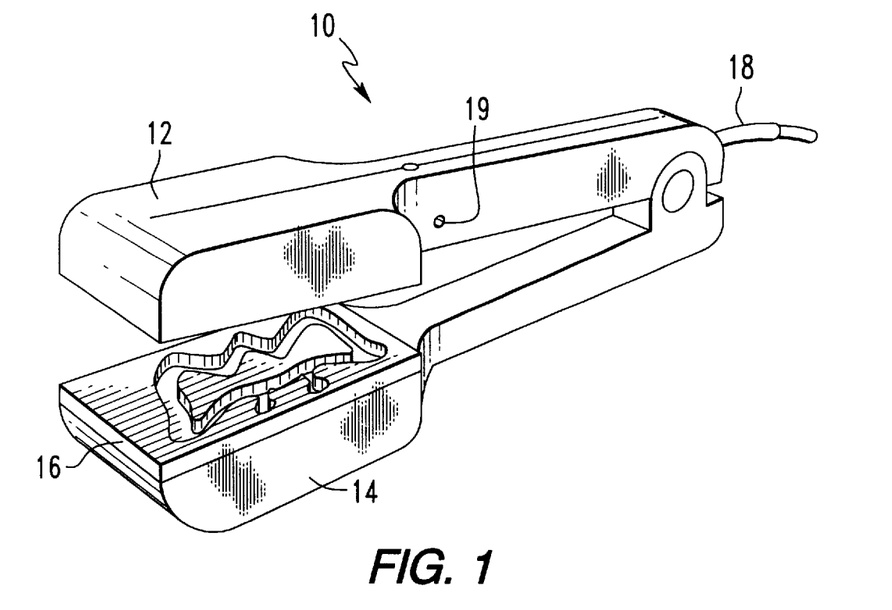
FIG. 1 is a perspective view of one preferred crimping iron of this invention.

FIG. 1 is a perspective view of one preferred thermal crimper 10 of this invention. Referring to FIG. 1, it will be seen that thermal crimper 10 is comprised of a top jaw 12 hingeably attached to a bottom jaw 14. A female die 16 is connected to the bottom jaw 14 and is adapted to engage a male die (not shown in FIG. 1) connected to top jaw 12. Electrical means (not shown) connected to a source of electricity 18 preferably heat the male and female dies during the operation of thermal crimper 10.

One may use any of the thermal crimping devices disclosed in the prior art. Thus, by way of illustration and not limitation, one may use one or more of the devices disclosed in U.S. Pat. Nos. 5,025,850, D316,762, D315,968, D315,967, D309,354, and the like. The disclosure of each of these United States patents is hereby incorporated by reference into this specification. Thus, by way of further illustration, one may use curling irons.

In one embodiment, the thermal crimper 10 is similar to the thermal crimper disclosed in U.S. Pat. No. 4,917,078 of Zaborowski, the entire disclosure of which is hereby incorporated by reference into this specification. The thermal crimper of this patent is a heatable hairstyling device which comprises: (a) a hand-grippable body section having a proximal end and a distal end; (b) a stationary hairstyling jaw member secured to said distal end of said body section and having an interiorly directed heatable plate surface, and (c) a movable hairstyling jaw member pivotally secured to said distal end of said body section having an interiorly directed member.

By way of further illustration, one may use the hair crimper disclosed in U.S. Pat. No. 4,870,250 of Rizzuto, the entire disclosure of which is hereby incorporated by reference into this specification. This Rizzuto patent discloses a device that includes a handle and pivoted upper and lower clamp halves thereon and electrical connections therein.

By way of yet further illustration, one may use the crimping iron sold by the Belson Products Company of Miami Lakes, Fla. as "GOLD'N HOT". This device may be utilized by removing the "goldtone crimping plates" which come with it and substituting applicant's novel male and female die plates.

Referring again to FIG. 1, and in the preferred embodiment depicted therein, it will be seen that the crimping device 10 depicted therein has been modified so that a hole 19 appears therein. This orifice 19 may be used to introduce hair dye (not shown) into the interior of the crimping device 10 so that it may contact the channels within the male and female dies.

Figure 2:
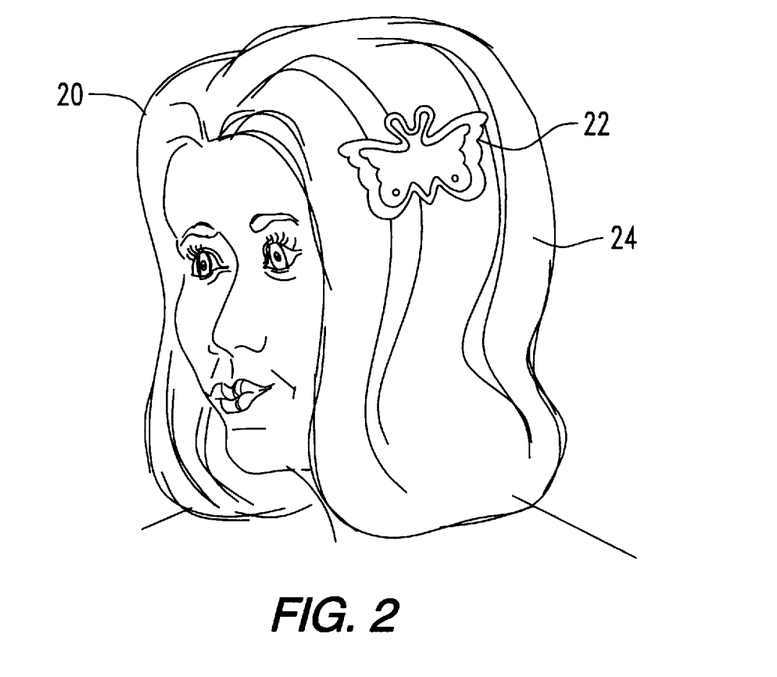
FIG. 2 is a perspective view of the crimped impression produced by the crimping iron of FIG. 1.

FIG. 2 is a perspective view of a user 20 with a thermally crimped and colored impression 22 in her hair 24.

Figure 3:
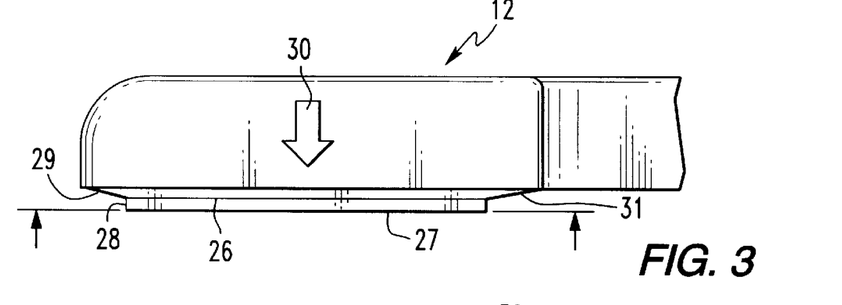
FIG. 3 is a partial side view of the top jaw of the crimping iron of FIG. 1.

FIG. 3 is a partial side view of jaw 12. Referring to FIG. 3, it will be seen that jaw 12 is connected to male die plate backing 26 integrally connected to die plate 28. In the embodiment depicted in FIG. 3, jaw 12 is moving in the direction of arrow 30. However, as will be apparent to those skilled in the art, when jaws 12 and 14 are hingeably attached to each other (see FIG. 1), arrows 30 and 32 will not necessarily be linear and parallel at all portions of the jaw travel. As will be apparent to those skilled in the art, however, the jaws 12 and 14 ultimately compress hair 24 between them (see FIG. 11).

Referring again to FIG. 3, it is preferred that male die plate backing 26 and die plate 28 consist essentially of a heat conductive metal such as, e.g., copper. The die plate assembly, in the embodiment depicted, contains chamfered edges 29 and 31.

Figure 4:
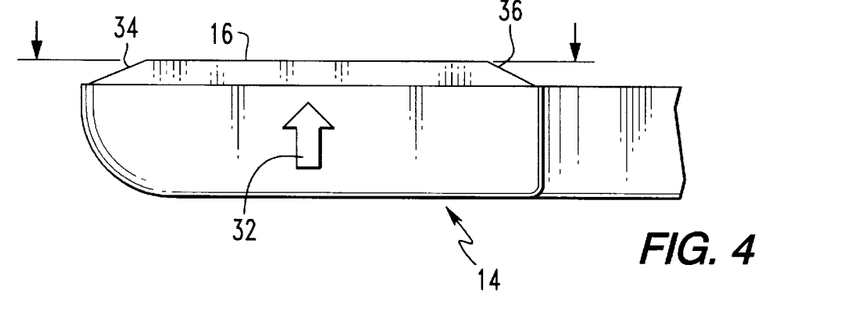
FIG. 4 is a partial side view of the bottom jaw of the crimping iron of FIG. 1.
Figure 5:
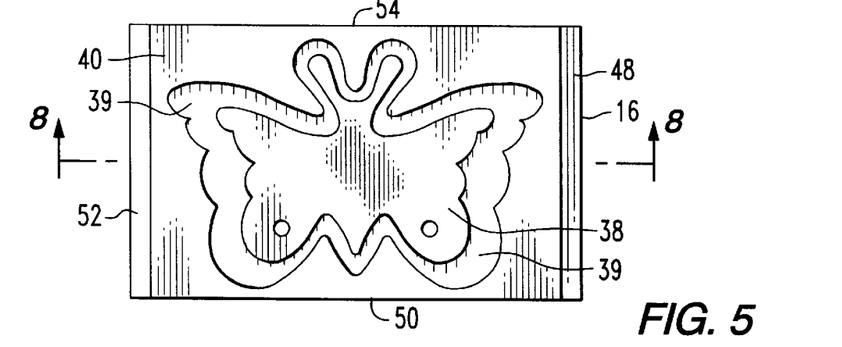
FIG. 5 is a top view of the female die plate of the crimping iron of FIG. 1.

FIG. 4 is a side view of a preferred lower jaw 14 which may be used in heat crimper 10. Referring to FIG. 10, and in the preferred embodiment depicted, it will be seen that female die plate 16 has at least two chamfered surfaces, surfaces 34 and 36. In one embodiment, not shown in FIG. 4, each of the surfaces of female die plate 16 has a chamfered edge. FIG. 5 is a top view of female die plate 16, which is comprised of an upwardly extending die 38. Upwardly extending die 38, which is in the shape of a butterfly in the embodiment depicted in FIG. 5, extends above backing plate 40. This feature is shown in more detail in FIG. 8.

Figure 7:
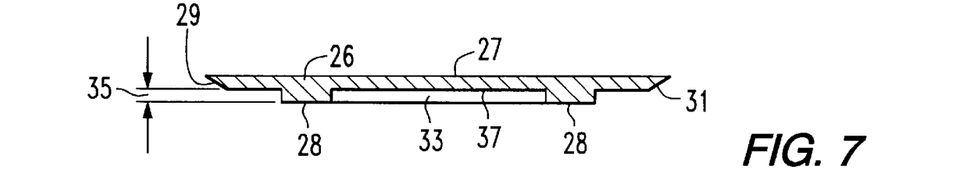
FIG. 7 is a schematic view illustrating how a user's hair is engaged by the male die plate of FIG. 6.

Referring to FIG. 7, it will be seen that protruding male 28 has a height 35 of from about 0.016 to about 0.093 inches, extending above the base 37 of recessed image 33.

Figure 8:
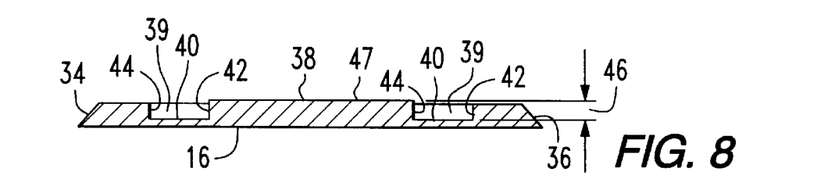
FIG. 8 is a schematic view illustrating how a user's hair is engaged by the female die plate of FIG. 5.

Referring to FIG. 8, it will be seen that upwardly extending die 38 is surrounded by a channel 39 defined by walls 40, 42, and 44. As will be apparent to those skilled in the art, a user's hair 24 (not shown in FIG. 8, but see FIGS. 1 and 2) will be compressed within channel 39 when jaws 12 and 14 are moved together.

Referring again to FIG. 8, the distance 46 by which the top wall 47 of die 38 extends above backing plate 40 is from about 0.032 to about 0.125 inches. In one embodiment, not shown, the height of the die 38 is less than the maximum height of the chamber 34 or 36.

Figure 12:
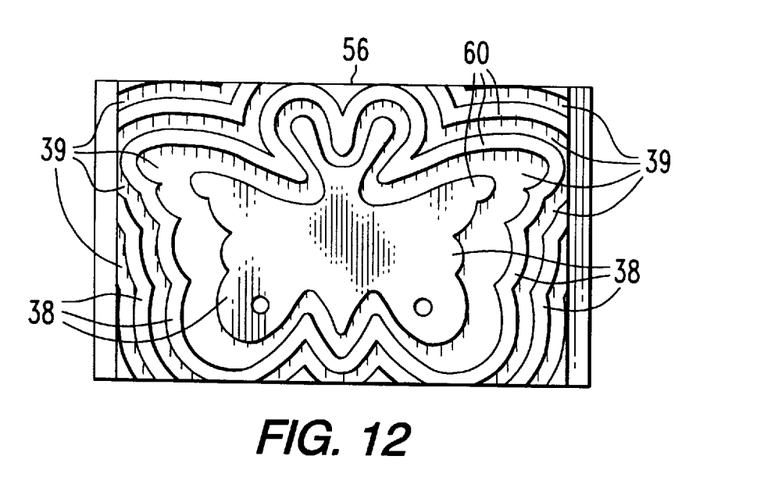
FIG. 12 is a top view of one female die plate of this invention.
Figure 13:
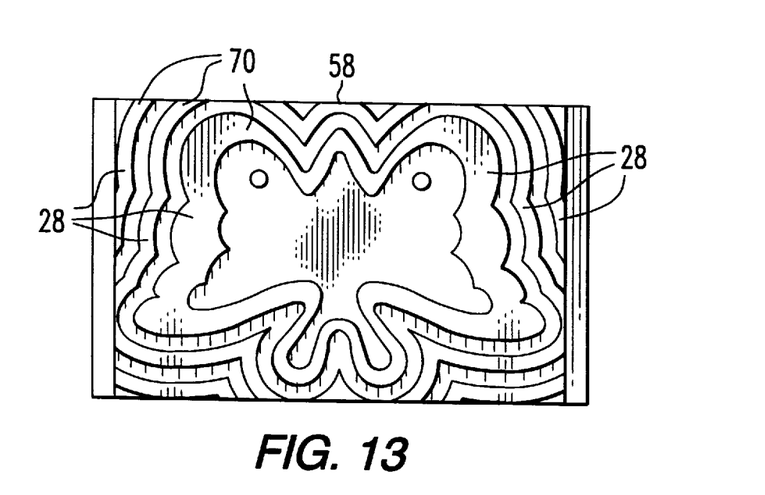
FIG. 13 is a top view of one male die plate of this invention.

Referring again to FIG. 5, and in the preferred embodiment depicted therein, each of walls 48, 50, 52, and 54 is chamfered. FIGS. 12 and 13 show similar chamfered structures for a female die member 56 and a male die member 58. As will be apparent to those skilled in the art, these die members are comprised of a series of substantially concentric areas 60 and 62 of continually decreasing height which form the chamfers.

In the embodiment depicted in FIG. 8, both the male die member 58 and the female die member 56 have two or more chamfered edges. In another embodiment, only the male member has such chamfered edges. In yet another embodiment, only the female member has such chamfered edges. In yet another embodiment, neither the male or female member has any chamfered edges.

Referring again to FIG. 6, and in the preferred embodiment depicted therein, it will be seen the die plate assembly 27, unlike the female die plate assembly 16, has an upwardly protruding die plate backing 26 which defines the perimeter of a recess image 33 with a complementary buttterfly shape as female die 38.

Figure 9:
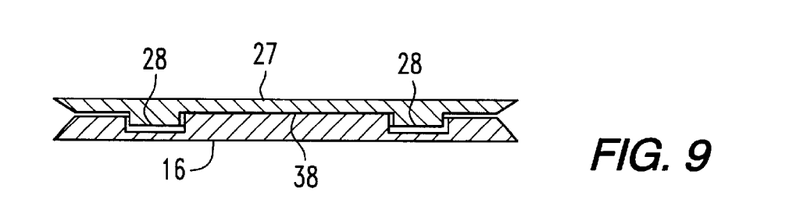
FIG. 9 is a schematic view illustrating how a user's hair is engaged when the male and female die plates are engaged with each other.

FIG. 7 is partial sectional view of male die plate assembly 27. FIG. 8 is partial sectional view of female die plate assembly 16. FIG. 9 illustrates how the two members 33 and 16 are disposed vis-a-vis each other when they are in contact.

Figures 10A, 10B:
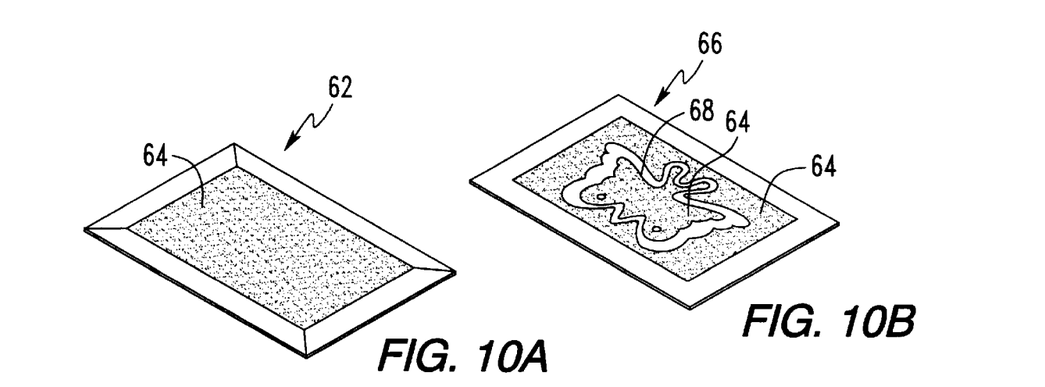
FIGS. 10A and 10B are top views of two different thermal transfer fabrics used in the device of FIG. 1.

FIG. 10A is a perspective view of a film or fabric 62 comprised of transferable hair color material 64. One may use any of the hair coloring chemicals or compositions known to those skilled in the art. Thus, by way of illustration and not limitation, one may use one or more of the hair colorings disclosed in U.S. Pat. Nos. 5,365,438, 5,273,739, 5,196,029, 4,834,767, 4,775,527, 4,211,247, and the like. The disclosure of each of these United States patents is hereby incorporated by reference into this specification.

In one embodiment, hair color material 64 may be "GLITTER GEL," which is a washable, water-based hair color sold by Jerome Russell Cosmetics of Chatsworth, Calif.; this material contains deionized water, sorbitol, propylene glycol, carbomer 940, triethanolamine, potassium sorbate, edta, quaternium-15, benzophenone-4, and fragance. In another embodiment, hair color material 64 may be one or more of the "STAR GAZER" "semi permanent conditioning hair colors" sold by Stargazer Products of London, England. Other suitable commercially available hair colors will be readily apparent to those skilled in the art.

Referring again to FIG. 10A, film or fabric 62 may be any suitable material from which color 64 is transferable by either pressure and or heat. By way of illustration and not limitation, film 62 may be made from fabric, parchment paper, other heat-resistant paper, etc.

In the embodiment illustrated in FIG. 10A, the entire top surface of film or fabric 62 consists of only one color material 64. In another embodiment, not shown, two or more of such coloring materials are used.

In the embodiment depicted in FIG. 10B, film 66 an outline of a butterfly 68 has been impressed within film or fabric 66, and color 64 is disposed in selected areas within the impression. The use of this film 66 will selectively transfer coloring agent to portions of the hair being treated.

It will be apparent to those skilled in the art that many different coloring agents, and/or many different combinations of coloring agents, may be disposed on all or selected portions of the films or fabrics 62 or 66.

Figure 11:
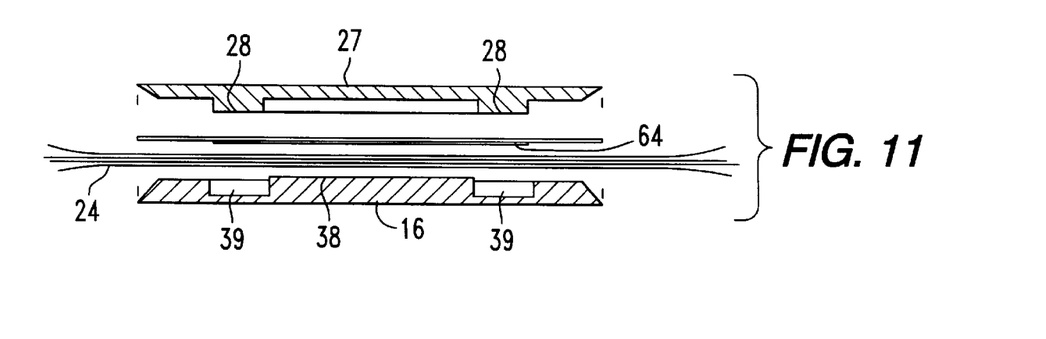
FIG. 11 is a schematic representation illustrating the interaction of the male die plate, the female die plate, the thermal transfer material, and the hair to be treated.

FIG. 11 is a schematic representation of the use of applicant's device. As will be apparent, the hair 24 to be treated will be compressed within channels 39, and be contacted with coloring agent 64, while be shaped by protruding dies 38 and 28. The resulting treated hair will not only be selectively colored, but it also will be shaped by the dies.

In one preferred embodiment, the film or fabric 62 is made from polytetrafluoroethylene. One may use one or more of the polytetrafluoroethylene films or fabrics known to those skilled in the art such as, e.g., one or more of the films disclosed in U.S. Pat. Nos. 5,622,565, 5,580,618, 5,578,131, 5,556,708, 5,546,889, 5,510,176, 5,504,37, 5,494,301, 5,489,370, 5,476,589, 5,468,531, 5,405,509, 5,358,678, 5,234,739, 5,217,666, 5,143,783, 4,985,296, 4,650,833, and the like. The entire disclosure of each of these United States patents is hereby incorporated by reference into this specification.

In one embodiment, the film or fabric 62 is a polytetrafluoroethylene liner such as, e.g. the liners disclosed in U.S. Pat. Nos. 5,577,741, 5,502,389, 5,480,455, 5,417,499, and the like. The entire disclosure of each of these United States patents is hereby incorporated by reference into this specification.

One prepared polytetrafluoroethylene fabric material is commercially available as "TEFLON BAKEWARE LINERS" from E. I. duPont deNemours and Company of Wilmington, Del. This material is a fluoropolymer/fiberglass based laminate which is prepared by coating a fiberglass substrate with fluoropolymer.

Other polytetrafluoroethylene-containing laminates may also be used. Thus, e.g., one may use one or more of the laminates described in U.S. Pat. Nos. 5,478,372, 5,466,531, 5,418,054, 5,393,929, 5,037,457, 4,212,923, 3,560,327, 3,486,961, and the like. The entire disclosure of each of these United States Patent Applications is hereby incorporated by reference into this specification.

In one preferred embodiment, the film or fabric 62 is a fabric material. As is known to those skilled in the art, a fabric is comprised of filaments, threads, or yarns. By way of illustration, some suitable polytetrafluoroethylene fabric materials include the fabric materials disclosed in U.S. Pat. Nos. 5,591,526 (PTFE fiber and fabric), 5,571,605 (PTFE fiber woven fabric), 5,549,966 (composite, commingled fiber of fiberglass and PFTE), 5,496,628 (a PTFE coated fiberglass substrate), 5,478,372 (fiberglass fabric with a layer of PTFE membrane laminated to the fabric surface), 5,468,923, 5,468,529, 5,456,983 (fiber of PTFE and fiberglass), 5,417,499 (a liner containing PFTE and polyester fiber), 5,399,418 (multiply textile fabric), 5,387,300 (PTFE yarn), 4,526,830 (coated woven or nonwoven fiberglass fabric), 4,347,278, 4,025,639, 4,015,038 (fiberglass fabric coated with PTFE), and the like. The entire disclosure of each of these United States patents is hereby incorporated by reference into this specification.

Figure 14:
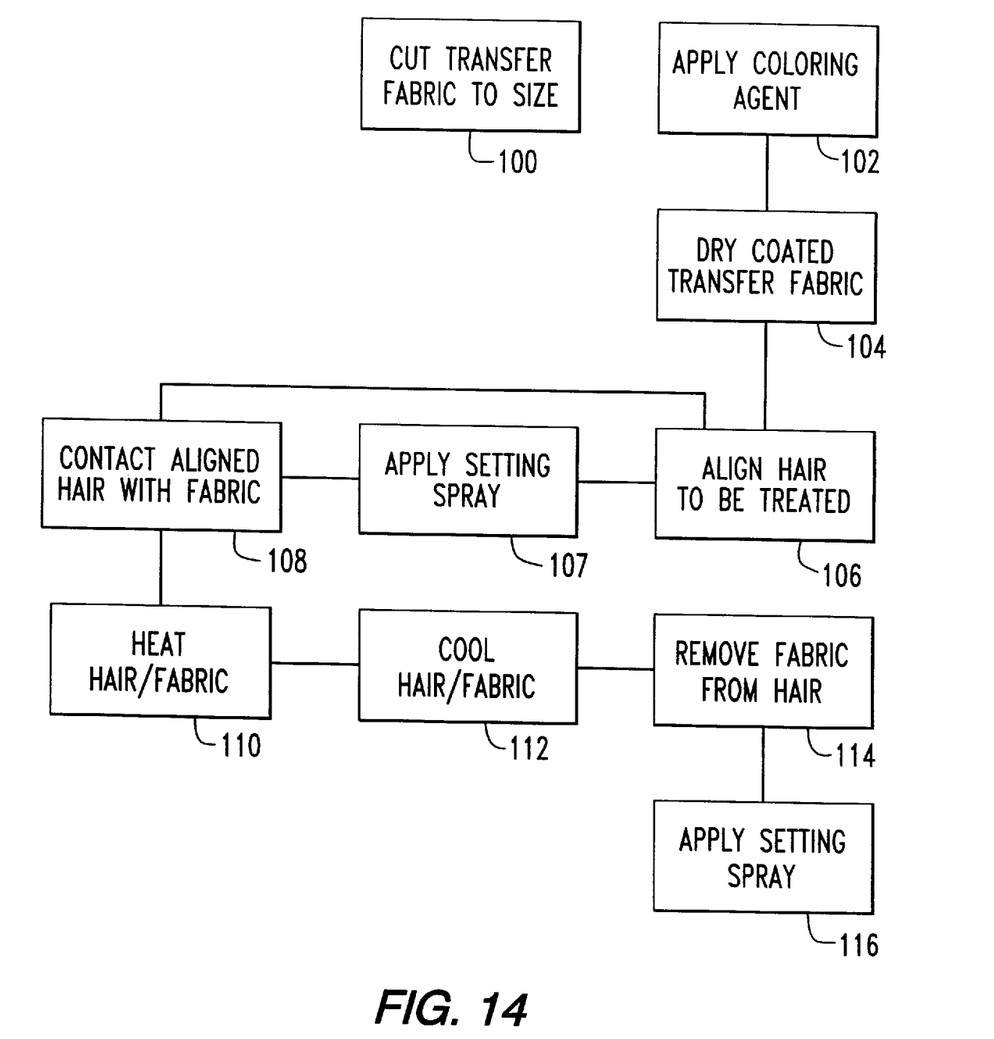
FIG. 14 is a flow diagram illustrating one preferred process of this invention.

FIG. 14 is a flow diagram illustrating one preferred process of the invention. Referring to FIG. 14, and in the preferred embodiment depicted therein, the transfer fabric 62 is cut to size. The fabric 62 generally should be cut into a desired shape with a surface area no larger than about 18 square inches and, preferably no larger than about 10 square inches. In one embodiment, it is preferred that the fabric 62 be cut into a substantially rectangular or square shape. In another embodiment, not shown, the fabric 62 is cut into a larger portion that covers a substantial part of the back of a prospective user's head.

In one embodiment, at least about one (and preferably at least about 4) holes are punched into the cut transfer fabric 62 so that the fabric may be properly aligned onto a plate with alignment pins. In another embodiment, the cut transfer fabric 62 is aligned onto said plate by means of double sided tape. In yet another embodiment, guide lines are imprinted upon the plate.

As is apparent to those skilled in the art, human hair is a class of textile fiber. Thus, e.g., the instant process may use food dyes mixed with citric acid or malic acid. One may also use basic dyes and salt, or textile dyes diluted with salts, detergents, and malic, citric, or tartaric acid. One may use, e.g., henna. See, e.g., pages 336–351 of Volume 4 of the McGraw-Hill Encyclopedia of Science and Technology (New York, N.Y. 1977).

The coloring agent maybe applied to the fabric 62 by conventional means such as, e.g., panting, silk-screening, printing, etc. As will be apparent to those skilled in the art, when more than one coloring agent is to applied, they preferably are separately applied.

Thereafter, in step 104, the coated transfer fabric 62 is dried by conventional means such as, e.g., hot air, infrared radiation, etc. Alternatively, or additionally, the coated transfer fabric may be sprayed with setting spray In one embodiment, the coloring agent is a washable material comprised of glitter. As is known to those skilled in the art, glitter-containing coloring agents are commercially available; see, e.g. U.S. Pat. Nos. 4,915,935 (reflective particles in foam matrix), 3,675,0005, and the like. The entire disclosure of each of these United States patents is hereby incorporated by reference into this specification.

By way of illustration, one may use the "scented body glitter" sold Townley Distributors; this material contains water, polyester glitter, propylene glycol, carbomer 940, triethanolamine, methylparaben, propylparaban, edta, and benzophenone-2.

By way of further illustration, one may use the "glitter cream gel" sold by Zauder Brothers, Inc. of Freeport, N.Y. This material contains purified water, propylene glycol, coated aluminum polyester film, carbomer-940, methylparaben, diavolidinyl urea, and propylparaban.

In step 106, the hair to be treated is aligned so that the individual hairs are substantially parallel to each other. This may be done by conventional means, such as brushing or combing such hair.

In step 107, which is optional, after the fabric 62 has been cut to the desired size, setting spray is applied to the hair to be treated. Alternatively, one may omit the setting spray step and go directly to step 108.

If a setting spray is used, it is preferred that a thermal active setting spray be used. In one embodiment, the setting spray described in U.S. Pat. No. 4,007,005 is used.

After the fabric 62 has been cut to the desired size, it is coated with coloring agent in step 102. In one embodiment, the preferred coloring agent is a water-soluble coloring agent such as, e.g., the hair coloring agents disclosed in U.S. Pat. Nos. 5,597,386 (water soluble coloring matter), 5,454,841 (water-soluble melanin), 5,281,240 (water soluble acid dyes), 4,981,485, 3,986,825, 3,973,901, 3,619,101 (water-soluble colored polymers), and the like. The entire disclosure of each of these United States patents is hereby incorporated by reference into this specification.

In the next step, step 108, the aligned hair is contacted with the surface of the fluoropolymer-containing fabric which is coated with coloring agent. Such contact may be effected by the means disclosed in FIG. 11. Alternatively, one may wrap the aligned hair and the fabric on a curling iron, waffle iron, and the like.

Thereafter, generally within a matter of seconds, the hair/fabric composite structure is preferably heated to a temperature of at least about 140 degrees Fahrenheit and, more preferably, at least about 180 degrees Fahrenheit in step 110. In one embodiment, the hair/fabric composite is briefly subjected to a temperature in excess of 300 degrees Fahrenheit. In another embodiment, the hair/fabric composite is subjected to pressure at ambient temperature.

It is preferred to subject the hair/fabric composite to the desired temperature for at least about 20 seconds. In one embodiment, the hair/fabric composite is heated for from about 30 to about 150 seconds.

Thereafter, in step 112, the treated hair/fabric composite is allowed to cool to ambient, generally over a period of from about 2 to 5 minutes. Thereafter, the fabric material is removed from the hair in step 114. Thereafter, hair spray or setting spray may optionally be applied in step 116.

The following examples are presented to illustrate the claimed invention but are not to be deemed limitative thereof. Unless otherwise specified, all temperatures are in degrees Fahrenheit.

EXAMPLE 1

Figure 6:
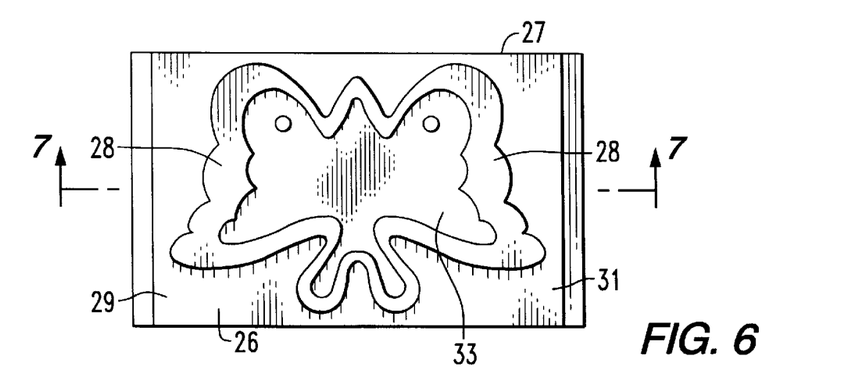
FIG. 6 is a top view of the male die plate of the crimping iron of FIG. 1.

In the experiment of this example, a crimping iron sold under the name of "BELSON GOLD'N HOT" by Belson Products of Miami Lakes, Fla. was modified by replacing the crimping plates with the male and female dies illustrated in FIGS. 5 and 6.

A color transferring fabric was prepared from commercially available bakeware liners sold by the E. I. duPont deNemours and Company as "TEFLON" commercial bakeware liners (TEFBO2). These fabric bakeware liners comprise a fiberglass substrate bonded to exterior layers of polytetrafluoroethylene. The TEFLON fabric was cut into rectangular shapes which were 4.5"'2.0".

The cut fabric sheets were then embossed with the male and female dies on the crimper to produce the butterfly pattern depicted in FIGS. 5 and 6. Thereafter, color was then applied to the indented portions of the fabric (see, e.g., sections 39 and 28 of FIGS. 5 and 6, respectively).

Onto 39 of the butterfly image (see FIG. 5) was painted a gold "GLITTER GEL" washable hair color which is sold by Jerome Russell Cosmetics of Chatsworth, Calif. Onto section 38 of the butterfly image (see FIG. 5) was painted a purple "GLITTER GEL" which also was obtained from the Jerome Russell Cosmetics company.

The painted butterfly images were allowed to air dry 36 hours. Thereafter, a fabric square containing one of these images was placed between the jaws of the Belson crimping iron so that the male die plate was above the colored section of the fabric and the colored section of the fabric was substantially congruent with the corresponding sections on the female die plate.

A young lady, about 26 years old, was used in this experiment; she had medium blonde hair. Her hair was washed with shampoo, rinsed, and dried to remove substantially all foreign matter from it. Thereafter, a section of her hair, roughly about 5 inches by about 1 inch, was combed at about a 35 degree angle while being held between a hairdresser's fingers.

The crimping iron was heated so that its jaws were at a temperature of about 180 degrees Fahrenheit. Thereafter, the combined hair was disposed between the jaws of the preheated crimping iron, and the jaws were closed in order to compress the hair and the fabric together. The jaws were held close for about 40 seconds.

Thereafter the jaws of the crimping iron were opened and pulled away from the subject's head; and the hair was gently allowed to drop to her head.

The hair was allowed to cool for two minutes. Thereafter, the fabric was removed from the hair.

Inspection of the hair revealed an indented portion of the hair that had been colored with gold and green glitter; the areas between the gold and green glitter were sharply demarcated.

EXAMPLE 2

The experiment of Example 1 was repeated, with the exception that the jaws were reversed. A raised, colored portion of hair was produced instead an indented portion.

EXAMPLE 3

The procedure of Example 1 was followed, with the exception that the central "body" area of the butterfly was colored with blue "STAR GAZER" conditioning hair color (obtained from Stargazer Products of London, England).

EXAMPLE 4

The procedure of Example 1 was followed with the exception that the modified BELSON crimping iron was returned to its original state with its original flat plates, and with the further exception that the image to be transferred was painted upon a non-embossed fabric sample. Although an indented impression was not obtained, a clearly defined, colored image was in fact transferred.

EXAMPLE 5

The procedure of Example 4 was followed with the exception that an image in the shape of a horse was transferred.

EXAMPLE 6

The procedure of Example 1 was followed with the exception an image of a "peace sign" was transferred. In the experiment of this example, red and blue "CRAYOLA" washable finger paints (sold by Binney & Smith, Inc. of Easton, Pa.) were used.

EXAMPLE 7

The procedure of Example 1 was substantially followed, with the exception that Zotos interchangeable flat and crimping iron (sold as model Z600 by Zotos International Corporation of Darien, Conn.) was used.

EXAMPLE 8

The procedure of Example 1 was substantially followed, with the exception that a Babyliss "pro convertible crimper and straightener in one" iron was used. This iron was obtained from the Babyliss Company of Belgium.

EXAMPLE 9

The procedure of Example 1 was substantially followed, with the exception that strips of colored fabric were disposed on the surface of a model 1182 curling iron sold by "Hot Tools, Inc.) of El Paso, Tex. In the experiment of this example, rectangular strips of colored fabric were applied to the hair so that the coloring material contacted the hair, and the curling iron was then wound around the hair to be colored.

EXAMPLE 10

The procedure of Example 9 was substantially followed, with the exception that a model 1110 curling iron from Hot Tools, Inc. was used, and the strips of colored fabric were in an elongated zig-zag shape.

EXAMPLE 11

The procedure of Example 9 was substantially followed, with the exception that a model 1181 curling iron from Hot Tools, Inc. was used. In this experiment, the strips contained multi-colored designs.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

I claim:

1. A process for removably applying coloring material to hair, comprising the steps of:
   (a) contacting a composite fabric material with hair, wherein:
      (1.) said composite fabric is a laminated structure comprised of a fiberglass substrate, and a top layer of polytetrafluoroethylene bonded to said fiberglass substrate, and (2.) said top layer of polytetrafluoroethylene is comprised of a top surface which is comprised of water-soluble coloring matter, and (3.) said water-soluble coloring matter contacts said hair, and (b) compressing said hair and said composite fabric material while heating said hair and said water-soluble coloring material to a temperature of at least about 140 degrees Fahrenheit.

2. The process as recited in claim 1, wherein said hair and said composite fabric material are compressed with a crimping device comprising a first jaw and a second jaw connected to each other.

3. The process as recited in claim 2, wherein said hair and said composite fabric material are heated to a temperature of at least about 180 degrees Fahrenheit.

4. The process as recited in claim 3, wherein said hair and said composite fabric material are heated to a temperature of at least about 300 degrees Fahrenheit.

5. The process as recited in claim 3, wherein:

(a) attached to said first jaw is a female die member comprising a first die plate which contains a channel extending around a substantially solid die member, and (b) attached to said second jaw is a male die member comprising a second die plate which contains a protruding portion extending around a substantially hollow die member.

6. The process as recited in claim 5, wherein each of said first die plate and said second die plate consists essentially of conductive metal.

7. The process as recited in claim 6, wherein said crimping device is comprised of means for heating said first die plate and said second die plate.

8. The process as recited in claim 7, wherein said first jaw and said second jaw are hingeably attached to each other.

9. The process as recited in claim 8, wherein said channel extending around said substantially solid die member is a continuous channel.

10. The process as recited in claim 9, wherein said hair coloring material is a washable hair coloring material.

11. The process as recited in claim 10, wherein said hair coloring material is a water-based material.

12. The process as recited in claim 11, wherein said hair crimping device comprises a hand-grippable body section.

* * * * *